United States Patent [19]

Rastelli et al.

[11] Patent Number: 5,475,150
[45] Date of Patent: Dec. 12, 1995

[54] ADSORBENT FOR THE SEPARATION OF ETHANOL FROM ETHYL TERT.-ALKYL ETHER

[75] Inventors: Henry Rastelli, New Fairfield, Conn.; Carmen M. Yon, Carmel, N.Y.; Stanley J. Frey, Palatine, Ill.

[73] Assignee: UOP, Des Plaines, Ill.

[21] Appl. No.: 337,805

[22] Filed: Nov. 14, 1994

Related U.S. Application Data

[62] Division of Ser. No. 201,590, Feb. 25, 1994, Pat. No. 5,401,887.

[51] Int. Cl.⁶ .................................................. C07C 41/34
[52] U.S. Cl. .......................................... 568/699; 568/697
[58] Field of Search .................................. 568/699, 697

[56] References Cited

U.S. PATENT DOCUMENTS

| | | | |
|---|---|---|---|
| 3,726,942 | 4/1973 | Louder | 260/683.61 |
| 4,219,678 | 8/1980 | Obenaus et al. | 568/697 |
| 4,447,653 | 5/1984 | Vora | 568/697 |
| 4,575,567 | 3/1986 | Vora | 568/697 |
| 4,605,787 | 8/1986 | Chu et al. | 568/697 |
| 4,857,664 | 8/1989 | Huang et al. | 568/695 |
| 4,876,394 | 10/1989 | Nagji et al. | 568/697 |

FOREIGN PATENT DOCUMENTS 542596A  10/1992  France.

*Primary Examiner*—Shean Wu
*Attorney, Agent, or Firm*—Thomas K. McBride; John G. Tolomei; Richard P. Silverman

[57] ABSTRACT

The present invention relates to a process for the separation of ethanol from a mixture thereof with ethyl tert.-alkyl ether employing a selective adsorbent comprising a mixture of sodium zeolite Y in combination with alumina wherein the percentage of the sodium zeolite Y ranges between 10 and 40 wt-%. The invention reduces the cost of this separation which is complicated by an azeotrope formation between the alcohol and the ether.

2 Claims, 2 Drawing Sheets

12345,475,150

1

ADSORBENT FOR THE SEPARATION OF ETHANOL FROM ETHYL TERT.-ALKYL ETHER

CROSS-REFERENCE TO RELATED APPLICATION

This application is a divisional of application Ser. No. 201,590, filed Feb. 25, 1994 now U.S. Pat. No. 5,401,887.

FIELD OF THE INVENTION

The present invention relates to a process for the production of ethers by the reaction of an alcohol with an isoalkene. More particularly, it relates to an improved process for the production of ethyl tert.-butyl ether (ETBE) by the reaction of ethanol with isoalkene. The invention specifically relates to improvements in the recovery and recycle to the reactor of unreacted ethanol without loss of ETBE product.

BACKGROUND OF THE INVENTION

The production of gasoline motor fuel requires consideration of the balance between the specifications provided by the automobile manufacturers and the concern for the environment as controlled by the governmental regulations on automobile emissions. Renewed environmental awareness and the desire for cleaner air on the part of the public has encouraged gasoline producers to develop reformulated grades of gasoline to reduce emissions from automobiles. Government has supported this reformulation initiative with new regulations which will result in the addition of oxygenates such as alcohols and ethers to the gasoline pool in an effort to reduce the level of CO and hydrocarbon emissions compared to emissions from conventional gasoline grades. The reformulated grades of gasoline, often referred to as oxyfuels, must meet all the typical gasoline specifications, and in addition must contain a minimum amount of oxygen. In the United States, according to current regulations, this oxyfuel must be sold in those areas of the country which do not meet minimum standards for ozone pollution.

Automotive gasoline is usually sold by a grade such as regular, or premium, according to its octane rating. This octane rating is a measurable quality and is derived from a laboratory measurement of octane number. The octane number is a rating of the performance of a sample of the gasoline in a standard test engine. Typically, two types of octane numbers are used to characterize the octane rating (i.e., a research octane (RON) and a motor octane (MON). These are determined separately according to well-known laboratory methods and averaged (RON+MON)/2 to provide an octane rating for a particular grade of gasoline.

Oxygen may be added to gasoline in the form of an oxygenate such as an alcohol including methanol, ethanol, or isopropanol and the like, or an ether including methyl tert.-butyl ether (MTBE), ethyl tert.-butyl ether (ETBE), tert. amyl-methyl ether (TAME), and the like. Oxygenates are added to the gasoline pool comprising hydrocarbons in mounts such that the octane rating and oxygen content of the blend increases, without exceeding vapor pressure limits. Vapor pressure is a physical property which reflects the amount of volatile material in the motor fuel. A high vapor pressure can result in hydrocarbon emissions to the atmosphere. Although alcohols such as methanol and ethanol have favorable octane numbers when blended with other gasoline components, the alcohols generally have a higher vapor pressure than ethers. Therefore, the gasoline producers have sought to increase the oxygen content of fuels by incorporating more renewable resource materials such as ethanol into the gasoline by converting the alcohols into ethers by combining the alcohols with $C_4$ and $C_5$ iso-olefins over an acid catalyst.

The production of ethers by the reaction of an iso-olefin and an alcohol is a well-known commercial operation. A number of detailed descriptions of such processes, particularly as they relate to the production of methyl tert.-butyl ether (MTBE) appear in the technical and patent literature. Exemplary of patent disclosures are U.S. Pat. No. 3,726,942 issued Apr. 10, 1973, to K. E. Louder; U.S. Pat. No. 4,219,678 issued Aug. 26, 1980, to I. Obenaus et at; U.S. Pat. No. 4,447,653 and U.S. Pat. No. 4,575,567 issued to B. V. Vora on May 8, 1984, and Mar. 11, 1986, respectively; and U.S. Pat. No. 4,876,394 issued to M. M. Nagji et al Oct. 24, 1989. These ethers are useful as high octane blending agents for gasoline motor fuels by virtue of their high Research Octane Number (RON) of about 120 and their low volatility.

MTBE has become the most commonly used ether for gasoline octane improvement. For example, a typical reformulated gasoline grade would require about 11 volume % MTBE to provide a gasoline containing about 2.0 wt % oxygen before reaching a vapor pressure limit. In a similar manner, if ETBE were used, the resulting blend with about 2.7 wt % oxygen would accommodate about 17 volume % ETBE at the same vapor pressure limit. ETBE has a higher octane value than MTBE and a blending vapor pressure of about one-half that of MTBE. In addition, ETBE like MTBE is miscible in gasoline in all proportions, but ETBE has a lower water solubility than MTBE, giving ETBE better fungibility in gasoline blends. ETBE is less likely than MTBE to be lost in pipeline transport. The cost of production is a major factor on the use of MTBE over ETBE. Methanol is typically derived from natural gas, while Ethanol is generally produced by fermentation of organic material. Given appropriate favorable price equalization of ethanol relative to methanol, the goal of encouraging the use of more regenerable material in the gasoline pool may be achieved. ETBE is produced by an etherification reaction of ethanol and an iso-olefin, such as isobutylene, wherein ethanol is present in an amount in excess of that required for the reaction. Typically, the reactor effluent is fractionated to produce a light stream comprising unreacted hydrocarbons and an ETBE product stream. Although some of the excess ethanol will be withdrawn with the unreacted hydrocarbon stream, at least a portion of the ethanol will remain in the ETBE product. The ethanol remaining in the ETBE product results in a loss of ethanol, and this ethanol significantly raises the vapor pressure and lowers the octane rating of the ETBE product. European Patent No. 542596 discloses the use of a costly and energy intensive extraction and three-stage fractionation scheme to separate the unconverted ethanol from the ETBE. Methods are sought to perform the separation of the ETBE from ethanol in the ETBE product in an efficient and low cost manner, without the loss of any valuable gasoline blending components.

SUMMARY OF THE INVENTION

It is the objective of the instant invention to provide a process for separating ETBE and other ethyl tert. -alkyl ethers from unreacted ethanol. The advantage of this process is that it provides an essentially pure ETBE, or ethyl tert. -alkyl ether product, containing less than about 100 ppm-wt ethanol. This purified ether product adds flexibility to the production and blending of reformulated gasolines and eliminates the octane and vapor pressure limitations caused by presence of azeotropic mixtures of ETBE and ethanol in the ETBE product.

In one embodiment, the invention is a cyclic process for preparing ethyl tert.-alkyl ethers comprising a series of steps. A reaction mixture formed by combining a feedstream comprising hydrocarbons having from 4 to 5 carbon atoms per molecule and containing isoalkene is combined with a near stoichiometric ratio of ethanol with respect to the isoalkene. The reaction mixture is contacted and reacted in a reaction zone to produce a reaction product effluent comprising ethyl tert. -alkyl ether, at least 10,000 ppm weight unreacted ethanol, and unreacted $C_4$-$C_5$ hydrocarbons. The reaction product effluent from the reaction zone is separated in a distillation column to provide an overhead effluent stream comprising unreacted ethanol and unreacted $C_4$-$C_5$ hydrocarbons, and a bottoms effluent stream comprising ethyl tert. -alkyl ether and unreacted ethanol. The bottoms effluent stream is passed to an adsorption zone containing a selective adsorbent to adsorb ethanol and an ether product stream comprising substantially pure ethyl tert.-alkyl ether is recovered. The selective adsorbent is regenerated with a regenerant stream to recover the ethanol to provide a recycle stream comprising ethanol, and the recycle stream is returned to the reaction zone.

In a further embodiment, the present invention is a cyclic process for preparing ethyl tert.-alkyl ethers comprising a series of steps. A feedstream comprising hydrocarbons having from 4 to 5 carbon atoms per molecule and containing isoalkene is combined with a near stoichiometric ratio of ethanol with respect to the isoalkene to provide a reaction mixture. The reaction mixture is contacted and reacted in a reaction zone to produce a reaction product effluent comprising ethyl tert.-alkyl ether at least 10,000 ppm weight unreacted ethanol and unreacted $C_4$-$C_5$ hydrocarbons. The reaction product effluent from the reaction zone is separated in a distillation column to provide an overhead effluent stream comprising unreacted ethanol and unreacted $C_4$-$C_5$ hydrocarbons, and a bottoms effluent stream comprising ethyl tert.-alkyl ether and unreacted ethanol. The bottoms effluent stream is passed to an adsorption zone containing a selective adsorbent to adsorb ethanol and recover an ether product stream comprising substantially pure ethyl tert.-alkyl ether. The overhead effluent stream is passed to a separation zone to provide an unreacted $C_4$-$C_5$ hydrocarbon stream depleted in ethanol and an unreacted ethanol stream. At least a portion of the unreacted $C_4$-$C_5$ hydrocarbon stream is passed to the adsorption zone to regenerate the selective adsorbent and to recover a hydrocarbon stream comprising ethanol. The hydrocarbon stream comprising ethanol is recycled to the separation zone.

In a still further embodiment, the present invention comprises a cyclic process for preparing ethyl tert.-alkyl ethers comprising a series of steps. A feedstream consisting essentially of hydrocarbons having from 4 to 5 carbon atoms per molecule and containing isoalkene is combined with a near stoichiometric ratio of ethanol with respect to the isoalkene to provide a reaction mixture. The reaction mixture is contacted and reacted in a reaction zone, preferably in the liquid phase, to produce a reaction product effluent comprising ethyl tert.-alkyl ether, at least 10,000 ppm weight unreacted ethanol, and unreacted $C_4$-$C_5$ hydrocarbons. The reaction product effluent from the reaction zone is separated in a distillation column. The distillation column contains at least a portion of the reaction zone. The distillation column provides an overhead stream comprising unreacted ethanol and unreacted $C_4$-$C_5$ hydrocarbons and a bottoms effluent stream comprising ethyl tert.-alkyl ether and unreacted ethanol. The bottoms effluent stream is passed to an adsorption zone containing a selective adsorbent. The selective adsorbent is selected from the group consisting of zeolite 13X, sodium zeolite Y, alumina, silicalite, and mixtures thereof to adsorb ethanol. An ether product stream comprising substantially pure ethyl tert.-alkyl ether is recovered from the adsorption zone. The overhead effluent stream is passed to a separation zone to provide an unreacted $C_4$-$C_5$ hydrocarbon stream depleted in ethanol and an unreacted ethanol stream. At least a portion of the unreacted $C_4$-$C_5$ hydrocarbon stream is passed to the adsorption zone to regenerate the selective adsorbent and to recover a hydrocarbon stream comprising ethanol. The hydrocarbon stream comprising ethanol is recycled to the separation zone.

DETAILED DESCRIPTION OF THE INVENTION

Figure 1:
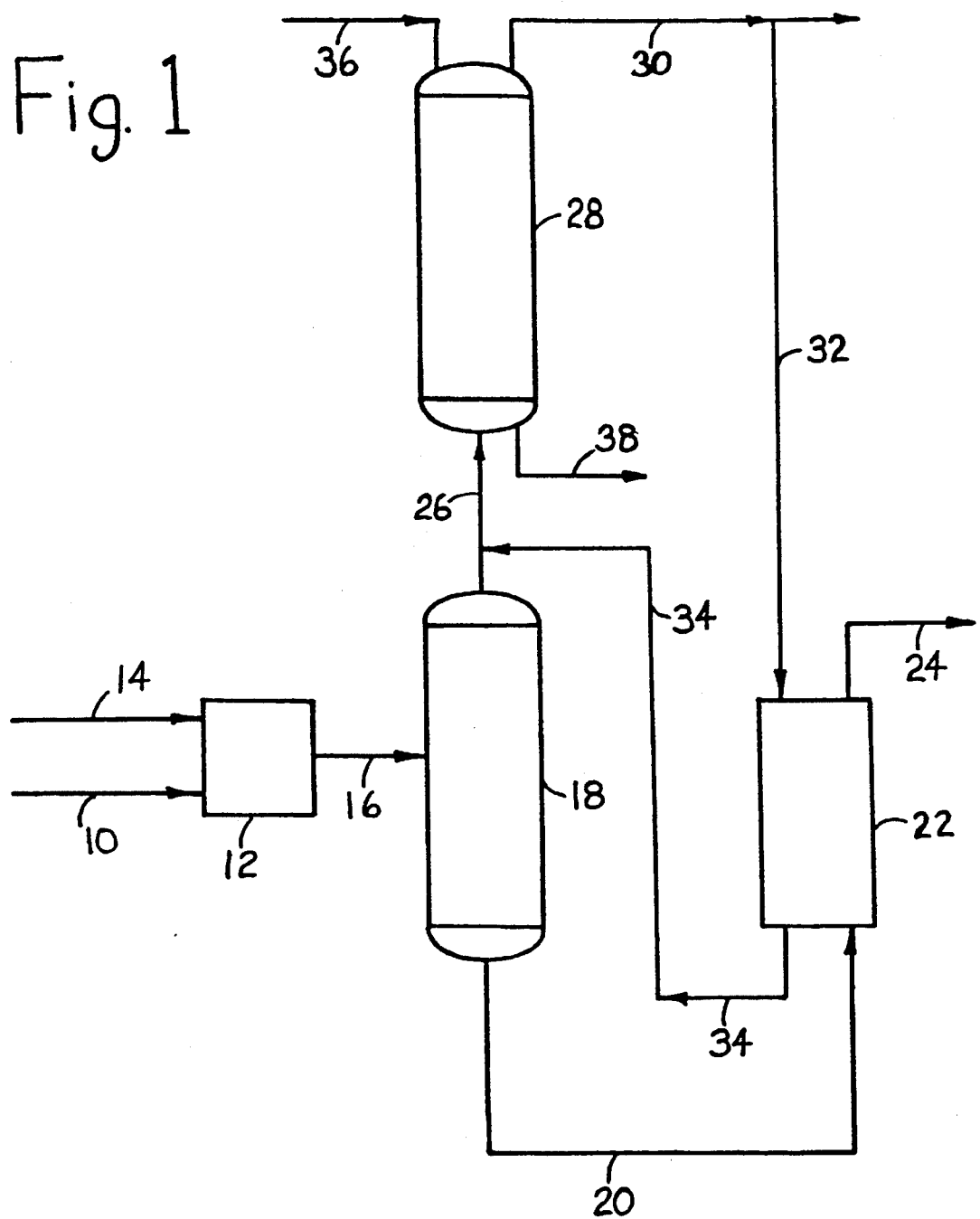
FIG. 1 is a schematic process flow design illustrating the process of the instant invention employing at least a portion of a water wash column raffinate to regenerate the adsorption zone.

The following description of the present process with respect to the production of ETBE is made with reference to the flow diagram of the drawing. In the interest of simplifying the description of the invention, the process system in the drawing does not contain the several conduits, valves, heat exchangers, and the like which in actual practice would be provided in accordance with the routine skill in the art to enable the process to be carried out on a continuous basis.

Ethanol in the liquid phase enters the reaction zone through line 10 and enters the reaction zone 12 along with a feedstream comprising $C_4$-$C_5$ hydrocarbons, preferably in a liquid stream, comprising isobutylene entering through line 14. Advantageously, all fluid streams introduced into the system have previously been dried to a water content of about 1 ppm-wt to about 10 ppm-wt water at the operating pressure of the reaction zone. Reaction zone 12 is operated at a temperature which in large measure is dependent upon the particular catalyst employed, but is generally in the range of about 40° C. to 90° C., and using an internal system pressure sufficient to maintain the reaction mixture in the liquid phase. In the present embodiment, the catalyst is of the ion-exchange resin type and the temperature of the reactor is about 60° C. The isobutylene-containing $C_4$-$C_5$ hydrocarbons include butene-1, cis and trans butene-2, butadiene, isobutane, n-butane, and n-amylenes along with isobutylene and isoamylenes. Preferably the isobutylene is present in an mount of at least 10 mole-% and preferably the near stoichiometric molar ratio of ethanol to isobutylene in the reaction zone ranges from about 0.95 to about 1.15. The effluent from the reactor comprises product ETBE, unreacted ethanol, unreacted $C_4$-$C_5$ hydrocarbons and diethyl ether in addition to other reaction by-products. This effluent is passed through line 16 to distillation zone 18. In some embodiments, the reaction zone may be made up of a first reaction zone outside of the distillation zone and a second reaction zone comprising at least a portion of the reaction zone contained within the distillation zone. In addition, the first reaction zone may be further subdivided into two or more stages with interstage cooling to remove heat and maintain the reaction in the liquid phase. While in this illustration the reactor and distillation column are represented as two different zones, relatively recent advancements have made possible the combination of the function of the reactor and the distillation column into a single apparatus, examples of which are taught in U.S. Pat. No. 5,243,102, which is hereby incorporated by reference. For purposes of the present invention, either operational mode is suitably employed. As a result of the distillation zone, a bottoms effluent stream 20 comprising ETBE is recovered from the bottom of distillation column 18. The bottoms effluent preferably contains from about 0.5 to about 7 weight percent of ethanol, and more preferably the bottoms effluent stream contains from about 5000 ppm-wt to about 2 wt % ethanol with the remainder being essentially ETBE, and is passed through line 20 to adsorption zone 22 containing a selective adsorbent which selectively adsorbs the ethanol. The selective adsorbent may be any of the commonly used solid adsorbents such as activated alumina, silicalite, silica gel or zeolitic molecular sieves. It has been found that zeolite X and Y molecular sieves offer particular advantages in adsorbing ethanol. More particularly, it was found that adsorbents such as zeolite sodium zeolite X, sodium zeolite Y, alumina, silicalite and mixtures thereof provide particular advantage for the selective adsorption of ethanol in the presence of ethyl tert.-alkyl ethers. The ether product, which is essentially pure ETBE, preferably containing less than 1000 ppm-wt, and more preferably containing less than 100 ppm-wt. ethanol, is removed from the adsorption zone through line 24. The overhead effluent stream from the distillation column 18 comprises about 0.7 to 1.5 wt % unreacted ethanol, unreacted $C_4$–$C_5$ hydrocarbons, 1 to 100 ppm diethyl ether as well as trace amounts of other volatile by-products. The content of the ethanol in the overhead effluent is dependent upon the formation of an azeotrope with the unreacted $C_4$–$C_5$ hydrocarbons. Thus, the amount of ethanol removed with the overhead effluent is limited by the formation of the azeotrope, and the remainder of the excess or unreacted ethanol is withdrawn in the bottoms effluent stream. This overhead effluent stream passes through line 26 to a separation zone, or water wash column 28, which adsorbs the ethanol. The non-adsorbed hydrocarbons, diethyl ether and other highly volatile impurities pass through water wash column 28 and, depending upon the intended utilization of this effluent, are optionally passed through line 30 to a second adsorbent bed (not shown) containing a selective adsorbent to produce a relatively pure $C_4$–$C_5$ hydrocarbon stream further depleted in ethanol. The particular selective adsorbent involved in the second adsorbent bed is also not a critical feature. Any of the commonly used solid adsorbents such as activated alumina, silica gel or zeolitic molecular sieves can be employed. It has been found that a sodium zeolite X is well suited to this application. Of the zeolite adsorbents, particularly zeolite 5A, zeolite 13X and zeolite D are preferred. More preferably zeolite 13X offers particular advantages in adsorbing trace amounts of oxygenates. In the present embodiment, on a cyclic basis, a portion of the $C_4$–$C_5$ hydrocarbon stream is passed through line 32 to the adsorption zone 22 as a regenerant for the adsorbent therein. The spent regenerant hydrocarbon stream comprising ethanol is returned to the water wash column 28 via lines 34 and 26. The substantially pure ethyl tert.-alkyl ether, or in this case ETBE, containing less than 100 ppm-wt ethanol, is recovered via line 24 for use in downstream processing or for blending into reformulated gasoline. A spent water wash stream is recovered from the water wash column in line 38. The spent water wash stream 38 may be passed to a water separation zone (not shown) for recovery of additional amounts of ethanol for recycle to the reactor 12 and for regeneration of the wash water for return to line 36. In an alternative operation, the overhead effluent stream in line 30 may be passed to a second adsorption zone (not shown) containing an adsorbent selective for the further removal of oxygenates from the overhead effluent, to provide an overhead effluent, containing unreacted $C_4$–$C_5$ hydrocarbons, with an oxygenate content of less than about 100 ppm-wt ethanol, prior to the use of at least a portion of the overhead effluent stream to regenerate the adsorption zone 22. The remainder of the overhead effluent stream may be passed to an alkylation zone for the production of alkylate or passed to a dehydrogenation zone for the production of additional amounts of iso olefin.

A wide variety of catalyst materials has been found to promote the etherification reaction including ion-exchange resins such as divinylbenzene cross-linked polystyrene ion exchange resins in which the active sites are sulfuric acid groups; and inorganic heterogeneous catalysts such as boric acid, bismuth molybdate, and metal salts of phosphomolybdic acids wherein the metal is lead, antimony, tin, iron, cerium, nickel, cobalt or thorium. Also boron phosphate, blue tungsten oxide and crystalline aluminosilicates of the zeolitic molecular sieve type have also been proposed as heterogeneous catalysts for the reaction of ethanol and isobutylene.

The reaction conditions are not narrowly critical and depend in large part upon the particular catalyst composition employed. Thus, both vapor phase and liquid phase processes have been proposed in which reaction temperatures are from about 50° C. to about 400° C., reaction pressures vary from about atmospheric to about 1.04 MPa (1500 psig) and stoichiometric molar ratios of ethanol to isoalkene range from 0.2:1 to about 10:1 and preferably, according to a near stoichiometric molar ratio ranging from about 0.95 to about 1.15. Thus, the present process may employ a near stoichiometric ratio of ethanol with respect to the isoalkene. Both batch type and continuous process schemes may be suitably employed. In the present process the reaction can be carried out in either the vapor phase or the liquid phase, but the liquid phase is preferred. For reaction zone portions within distillation zones, the reaction proceeds primarily in the liquid phase. Isobutylene is the preferred isoalkene, although isoamylene may also be employed.

The selective adsorbent for the process of the present invention will be understood by those skilled in the art to be any of the well-known adsorbents for selectively adsorbing ethanol from a mixture thereof with ethyl tert.-alkyl ethers such as ETBE, and the adsorbents can be employed whether in simple or in compound bed, provided only that these adsorbents exist and that they be maintained at a capacity for adsorbing essentially all of the ethanol from the distillation column bottoms to produce ETBE in the desired purity. A number of the typical adsorbents such as zeolite 4A and 5A were considered for the instant process, but were found to adsorb the ethanol too strongly to be regenerated completely. Silica gel was also considered, but silica gel was found not to be selective enough to adsorb much of the ethanol in the presence of ETBE. Silicalite was surprisingly found to provide a good capacity for the adsorption of ethanol with a relatively sharp mass transfer zone. A mixture of sodium zeolite Y in combination with alumina, similar to the adsorbents described in U.S. Pat. No. 4,725,361 to Fleming for the removal of trihalomethane from aqueous solutions, also was surprisingly found to exhibit high capacities for ethanol with a relatively sharp mass transfer zone and with the ability to be regenerated by a non-reactive gas or liquid. It is believed that when the proportion of the sodium zeolite Y in the adsorbent mixture, ranges preferably between 10 and 40 wt percent of the mixture, and more preferably when the proportion of sodium zeolite Y ranges between 15–30 wt %, the resulting adsorbent becomes isostructural, thus moderating the strength of the adsorbent by redistributing the number of sodium cations coming in contact with the ethanol. This isostructural form permits the adsorbent mixture to retain a high capacity and selectivity for the ethanol, but lowers the strength of the adsorbent mixture to permit the adsorbent admixture to be desorbed or regenerated with either a gas phase, or a liquid phase regenerant. Zeolite 13X also was found to have a high initial capacity for ethanol in the presence of ETBE; however, some degradation of adsorbent capacity was observed following subsequent regeneration. In commercial service, zeolite 13X should provide performance within an acceptable range. Thus, silicalite, zeolite 13X, sodium zeolite Y, alumina and mixtures thereof are preferred for use as the selective adsorbent with the instant invention when configured either as separate beds or in compound beds having multiple layers of adsorbents.

Figure 2:
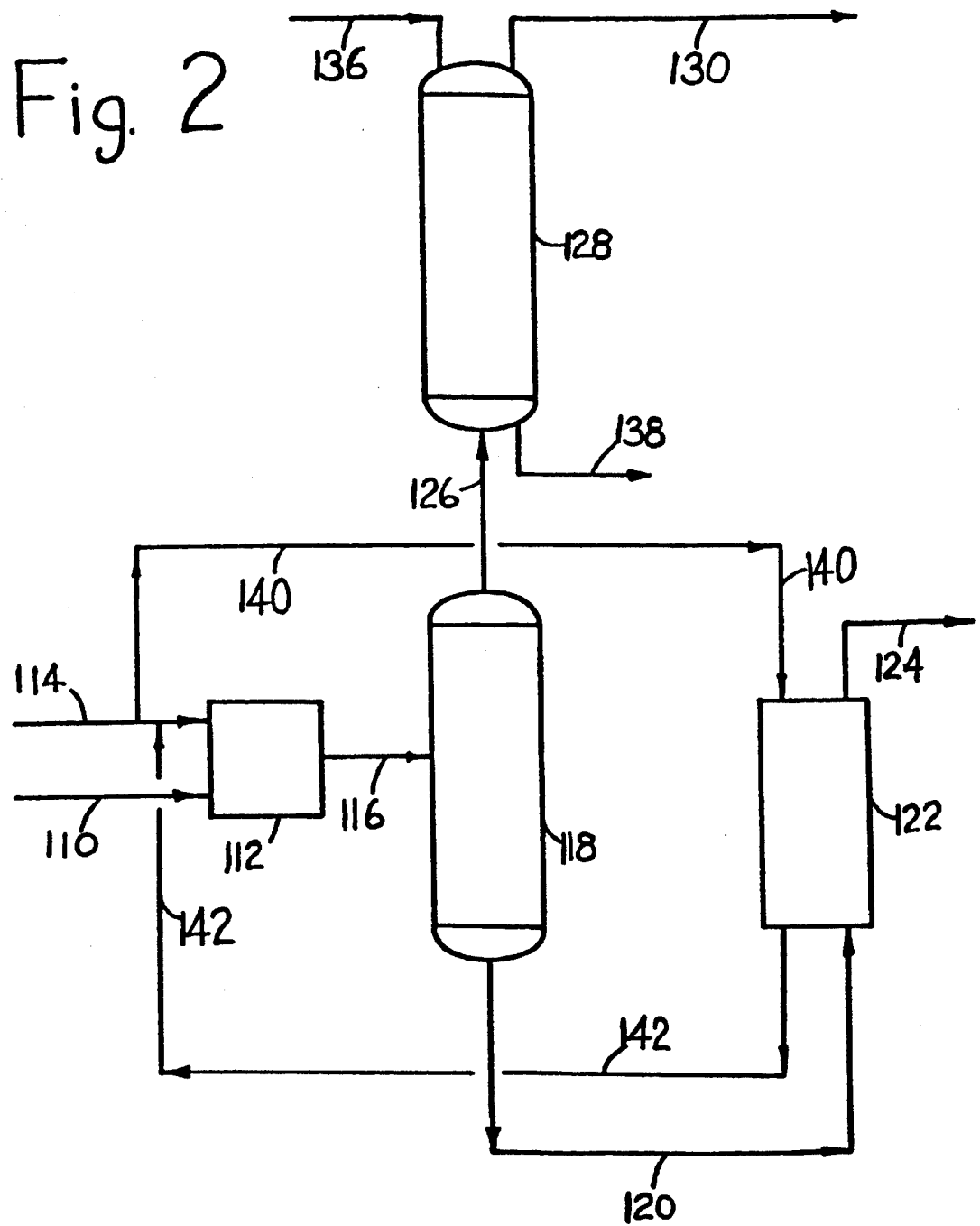
FIG. 2 is a schematic process flow diagram illustrating an alternate embodiment of the invention employing a portion of the feedstream to regenerate the adsorption zone.

FIG. 2 illustrates an alternate embodiment of the instant invention. The ethanol is passed to the reaction zone 112 in line 110. A feedstream comprising $C_4$–$C_5$ hydrocarbons including at least some proportion of isobutylene is passed to reaction zone 112 via feed header 114. The reaction zone 112 contains a catalyst to produce a reaction product effluent comprising ethyl tert.-alkyl ether such as ethyl tert.-butyl ether, which is withdrawn from the reaction zone 112 and passed in line 116 to a distillation column 118. The distillation column 118 separates the reaction product effluent into an overhead effluent stream 126 comprising unreacted $C_4$–$C_5$ hydrocarbons and a bottoms effluent stream 120 comprising ethyl tert.-alkyl ether and unreacted ethanol. The bottoms effluent stream 120 is passed to an adsorption zone 122 comprising at least two adsorption beds containing an adsorbent as described hereinabove and selective for the adsorption of ethanol. An essentially pure ethyl tert.-alkyl ether product is withdrawn in line 124 for subsequent use in downstream processing or gasoline blending to produce reformulated gasoline. The adsorbent zone is periodically regenerated on a cyclic basis with at least a portion of the feedstream withdrawn from the feed header 114 in line 140 and passed to the adsorption zone 122. A spent regenerant stream 142 comprising unreacted ethanol is recycled to the reaction zone 112 via line 142 which returns the recycle stream to the feed header 114 prior to the reaction zone. The distillation column overhead effluent stream 126 is passed to a water wash column, or separation zone, 128 wherein the overhead effluent stream is contacted with a water wash stream 136 to provide an unreacted $C_4$–$C_5$ hydrocarbon stream 130, depleted in ethanol comprising less than 500 ppm-wt ethanol and a spent water wash stream 138.

The temperature within the adsorption beds of the adsorption zone is preferably within the range, initially, of about 30° C. to 50° C., i.e., essentially the same as the temperature of the effluent from the fractionation (distillation) tower. The pressure in the beds is preferably maintained such as to cause the streams being treated to remain in the liquid phase. The regeneration of the beds is accomplished in the conventional manner by purging, preferably in a direction countercurrent to the direction of flow through the beds during the adsorption step therein. The purge stream, preferably in the liquid phase, is advantageously of the same or similar composition as the $C_4$–$C_5$ hydrocarbon stream feed to the etherification reactor. The temperature of the purge stream is not narrowly critical, but should be at least greater than the temperature of the feedstream being treated during the adsorption step, and is preferably at least 30° C. to 150° C. higher.

The following examples are only used to illustrate the present invention and are not meant to be limiting.

EXAMPLES

Example I

A stainless steel adsorbent column (approximately 6.4 mm (¼ inch)×10 mm (4 inch) was filled with about 1.5 grams of adsorbent pellets having a particle size of about 177 to about 250 microns (60–80 mesh) and was employed in a series of adsorption and regeneration tests to evaluate the suitability of a series of adsorbents for removing ethanol from ETBE in a liquid solution thereof and regenerating the adsorbent with a heated inert gas (helium) or hydrocarbon vapor (n-hexane). The liquid solution of ethanol in ETBE was a commercial sample obtained from an ETBE production facility with the azeotropic composition comprising about 2.2 wt-% ethanol. During the adsorption step, the ethanol/ETBE solution was pumped with a low flow rate, positive displacement pump (Waters 510 HPLC) through the adsorbent column and 1 cc samples of the adsorption effluent were collected for 10 seconds in sealed vials at 30 second intervals for a period of up to about 5 minutes. During the regeneration step with helium, helium gas was passed through the column while gradually heating the column from about ambient temperature to about 230° C. over a period of about 10 minutes. The passing of the helium gas at 230° C. was continued for an additional period of 10 minutes. The adsorption column was allowed to cool to ambient conditions. The adsorption column was weighed after the adsorption step and after the regeneration step to determine the amount of material adsorbed or desorbed. When hydrocarbon vapor regenerant was employed, the hydrocarbon was vaporized at 230° C. and passed through the adsorbent column. The vapor flow was continued for about 60 minutes while effluent was collected at periodic intervals. The adsorption column was then isolated and cooled to ambient conditions. The samples were analyzed by gas chromatography and the analyses were plotted with time at the mean time during which the sample was taken to determine the ethanol breakthrough time and the stoichiometric time. The breakthrough time is determined when the ethanol concentration in the effluent reached 5% of the feed composition and the stoichiometric time is based on the time when the effluent is at 50% of the feed concentration. Table 1 presents the results of this experimental procedure for fresh activated adsorbent. The following adsorbents were considered: silicalite, zeolite 13X, zeolite 4A, zeolite 5A, silica gel and an adsorbent comprising caustic treated alumina and about 13 wt-% sodium Y zeolite. (Alumina/NaY)

TABLE 1

| | FRESH ADSORBENT CAPACITY | | |
|---|---|---|---|
| Adsorbent | Breakthrough Loading, wt-% | Stoichiometric Loading, wt-% | Weight of Unused Bed, % |
| Silicalite | 6.0 | 7.2 | 17 |
| 13X | 10.5 | 13.0 | 19 |
| 4A | 1.0 | 2.3 | 57 |
| 5A | 4.4 | 7.9 | 44 |
| Silica Gel | 2.2 | 4.8 | 54 |

TABLE 1-continued

FRESH ADSORBENT CAPACITY

| Adsorbent | Breakthrough Loading, wt-% | Stoichiometric Loading, wt-% | Weight of Unused Bed, % |
|---|---|---|---|
| Alumina/NaY | 9.1 | 11.1 | 18 |

These results show that silicalite, 13X and the Alumina/NaY mixture demonstrate significant capacity (greater than 6.0%) for adsorbing ethanol from mixtures of ETBE and ethanol.

The weight of unused bed, WUB, for the tube of Example 1 is determined experimentally from the following equation:

$$\frac{WUB}{\text{Weight of Bed}} \times 100\% = 100 \times 1 - \frac{\text{breakthrough time}}{\text{stoichiometric time}}$$

The weight of unused bed, WUB, is a measure of the sharpness of the mass transfer zone. The lower the WUB, the more efficient is the use of adsorbent for the separation in the experimental column. Surprisingly, silicalite, 13X and the Alumina/NaY mixture displayed the lowest values of WUB and are therefore preferred for the adsorption of ethanol from mixtures thereof with ETBE in the present invention.

Examples II

The adsorption and regeneration steps of Example I were repeated following the regeneration of the samples of some adsorbents tested in Example I. The regeneration was carried out with helium, an inert gas, at 230° C. as described in Example I. The results following this first cycle are shown in Table 2.

TABLE 2

ADSORBENT CAPACITY AFTER FIRST CYCLE

| Adsorbent | Breakthrough Loading, wt-% | Stoichiometric Loading, wt-% | Weight of Unused Bed, % |
|---|---|---|---|
| Silicalite | 7.4 | 8.4 | 12 |
| 13X | 8.7 | 11.2 | 22 |
| 4A | 0.5 | 1.5 | 67 |
| 5A | 1.2 | 2.8 | 57 |
| Silica Gel | 2.3 | 5.1 | 55 |
| Alumina/NaY | 8.3 | 10.4 | 20 |

The adsorbent capacity for silicalite, 13X and the Alumina/NaY mixture showed some reduction in cycled capacity with a consistently sharp mass transfer zone as evidenced by the weight of unused bed remaining below about 20%. The 4A and 5A zeolites showed significant capacity reductions after one cycle, while the relatively weak and non-selective capacity of the silica gel adsorbent remained essentially the same with a long transfer zone.

Example III

After the second or third regeneration cycle with helium according to the procedure described in Example I, a regeneration step using hexane vapor was employed. Pure n-hexane was employed to simulate the use of a hydrocarbon stream more consistent with industrial practice which may have some coadsorption effect. The results of this vapor phase hydrocarbon regeneration are shown in Table 3.

TABLE 3

ADSORBENT CAPACITY AFTER N-HEXANE REGENERATION

| Adsorbent | REGEN Cycle # | Breakthrough Loading, wt-% | Stoichiometric Loading, wt-% | Weight of Unused Bed, % |
|---|---|---|---|---|
| Silicalite | 4 | 4.9 | 6.1 | 20 |
| 13X | 4 | 7.5 | 13.9 | 46 |
| Alumina/NaY | 4 | 8.2 | 10.2 | 20 |

The silicalite results indicated that the hexane regeneration caused a loss of capacity and a lengthening of the mass transfer zone. Because hexane is a non-polar material which should be a preferred adsorbate for silicalites, it appears that the ethanol is unable to easily displace the residual hexane, resulting in a lower breakthrough loading and a longer mass transfer zone.

The use of hexane with 13X restored the capacity of the 13X to fresh capacity. However, the more difficult displacement of the n-hexane by ethanol appears to have resulted in a much longer mass transfer zone than with the helium regeneration of Example II. The use of n-hexane to regenerate the Alumina/NaY mixture restored the capacity without any change in the mass transfer zone.

Example IV

The procedure of Example I for the regeneration with n-hexane was modified by not heating the regenerant and employing the n-hexane as a liquid at room or ambient conditions. This test was performed on the Alumina/NaY sample, following the vapor regeneration of Example III. The amount of ethanol desorbed from the Alumina/NaY material comprises one third of the adsorption capacity. Thus, liquid phase regeneration of the alumina/NaY adsorbent surprisingly also can be employed but at a reduced capacity (⅓ of a heated regeneration).

Example V

A series of Cases for the etherification of a hydrocarbon feed and the subsequent recovery of an ethanol free ETBE product are shown in Table 4. These were calculated from engineering design consideration and based on the performance of the 13X adsorbent in Example I. In all cases the regeneration was accomplished with a liquid regenerant at 110° C. followed by cooling, and the ETBE product from the adsorption zone contained less than about 100 ppm-wt of ethanol. The flow schemes considered employed either a separate conventional etherification reaction zone and a distillation column, or a reaction with distillation, RWD, scheme wherein at least a portion of the etherification zone is contained in the distillation column.

TABLE 4

REACTOR EFFLUENT

| CASE | FEED | REACTION ZONE | STOICHIO-METRIC RATIO | FEED % ISOBUTYLENE | Wt-% Ethanol OVERHEAD | Wt-% Ethanol BOTTOMS |
|---|---|---|---|---|---|---|
| A | FCC | CONV | 1.01 | 15 | 1.5 | 1.65 |
| B | FCC | RWD | 1.10 | 15 | 1.5 | .66 |
| C | DEHYDRO | RWD | 1.03 | 45 | 0.7 | 1.6 |
| D | DEHYDRO | RWD | 0.95 | 45 | 0.7 | .67 |

Case A, Table 4, represents the processing of about 45M metric tonnes/hour (100,000 lb/hr) of a $C_4$ hydrocarbon feed from an FCC unit in a conventional etherification unit followed by the separation of the reactor effluent in a distillation column as shown in FIG. 2. The reactor was operated at an olefin conversion of 97%, and the ratio of ethanol to iso-alkene in the feed to the etherification reactor was 1% over the stoichiometric ratio. A three-bed adsorption system was employed for the removal of the 1.65% ethanol from the ETBE product, wherein each bed contained about 1.36 metric tons (3000 lb) of 13X adsorbent. The regeneration of the ethanol adsorption beds was accomplished with about a 40% fraction of the feed; although about half of the distillation overhead could also be employed as the regenerant following a water wash step as shown in FIG. 1.

Case B of Table 4 represents the processing of the same feed as Case A in an etherification unit wherein the distillation column contains an etherification reaction zone, operating at 98% olefin conversion with a stoichiometric ratio of ethanol to iso-olefin of 1.1. The resulting distillation column bottoms contained about 0.66 wt % ethanol as sent to a three-bed adsorption unit for the removal of the ethanol from the ETBE product. Each of the three adsorption beds contained about 0.9 metric tonnes (2,000 lb) of 13X adsorbent. The regeneration of the adsorbent beds was carried out with about a 27 percent of the feed, although about 30 percent of the water washed distillation column overhead, comprising the unreacted $C_4$–$C_5$ hydrocarbons, also could be employed as the regenerant.

In case C, about 91M metric tonnes/hour (200,000 lb/hr) of a hydrocarbon feed comprising $C_4$ hydrocarbon derived from a butane dehydrogenation process was passed to an etherification reaction zone and a distillation column wherein at least a portion of the distillation column contained second etherification reaction zone at an overall olefin conversion of 98% and a stoichiometric ratio of ethanol to iso-olefin of about 1.03. The resulting distillation column bottoms comprised about 0.67 wt-% ethanol. The distillation column bottoms was sent to a three-bed adsorption unit wherein each of the adsorption bed contained about 10.4 metric tonnes (23,000 lb) of 13X adsorbent. In this case C, almost all of the available feed was required to regenerate the adsorption beds. The results of this case C suggested that for this application, the etherification reaction zone should be operated at a lower stoichiometric ratio, even slightly sub-stoichiometric.

Case D represented the same feed and reaction zone configuration of Case C, operated at a sub-stoichiometric ratio of 0.95 and at a corresponding olefin conversion of about 92%. The adsorption zone is the same as that of Case C; however, in Case D, the adsorption beds may be regenerated with essentially all of the water washed distillation column overhead.

What is claimed is:

1. A process for the separation of ethanol from a mixture thereof with ethyl tert.-alkyl ether employing a selective adsorbent comprising an adsorbent mixture of a sodium zeolite Y in combination with alumina wherein the percentage the sodium zeolite Y ranges between 10 and 40 wt-%.

2. The process of claim 1 wherein the percentage of sodium zeolite Y in said adsorbent mixture ranges from 15 to 30 wt-%.

* * * * *